United States Patent
Fleischer-Trebes et al.

(10) Patent No.: US 10,998,086 B2
(45) Date of Patent: May 4, 2021

(54) METHOD FOR CONFIGURING A PRODUCTION PLANT DESIGNED FOR PERFORMING AT LEAST ONE CHEMICAL REACTION

(71) Applicant: BAYER AKTIENGESELLSCHAFT, Leverkusen (DE)

(72) Inventors: Christoph Fleischer-Trebes, Essen (DE); Bojan Niko Broetz, Essen (DE)

(73) Assignee: BAYER AKTIENGESELLSCHAFT, Leverkusen (DE)

( * ) Notice: Subject to any disclaimer, the term of this patent is extended or adjusted under 35 U.S.C. 154(b) by 951 days.

(21) Appl. No.: 15/527,693

(22) PCT Filed: Nov. 20, 2015

(86) PCT No.: PCT/EP2015/077243
§ 371 (c)(1),
(2) Date: May 17, 2017

(87) PCT Pub. No.: WO2016/083262
PCT Pub. Date: Jun. 2, 2016

(65) Prior Publication Data
US 2018/0307802 A1    Oct. 25, 2018

(30) Foreign Application Priority Data
Nov. 24, 2014   (DE) ..................... 10 2014 117 122.5

(51) Int. Cl.
*G05B 13/02*     (2006.01)
*G16C 20/10*     (2019.01)
(Continued)

(52) U.S. Cl.
CPC ....... *G16C 20/10* (2019.02); *G05B 19/41845* (2013.01); *G05B 23/0213* (2013.01);
(Continued)

(58) Field of Classification Search
CPC .. G16C 20/10; G16C 20/40; G05B 19/41845; G05B 23/0213; G05B 2219/25083;
(Continued)

(56) References Cited

U.S. PATENT DOCUMENTS 7,526,347 B2 *   4/2009   Lucas ................ G05B 19/0426
                                                           700/79
8,135,481 B2 *   3/2012   Blevins .............. G05B 19/0426
                                                           700/51
(Continued)

FOREIGN PATENT DOCUMENTS

CN    101371164 A    2/2009
CN    101887544 A   11/2010
CN    102354377 A    2/2012

OTHER PUBLICATIONS

"System 800xA the Power of Intergration: 800xA Device Management and Fieldbus Overview", (2010) pp. 1-16, XP055082479.
(Continued)

*Primary Examiner* — Ramesh B Patel
(74) *Attorney, Agent, or Firm* — McBee Moore & Vanik IP, LLC

(57) ABSTRACT

Method for configuring a production plant designed for performing at least one chemical reaction, wherein the production plant has at least one plant module, and a plant module for configuring the production plant, which plant module is chosen from a module database running on a first server system and/or is combined from a component database running on a second server system.

9 Claims, 2 Drawing Sheets

(51) Int. Cl.
  *G16C 20/40* (2019.01)
  *G05B 23/02* (2006.01)
  *G05B 19/418* (2006.01)

(52) U.S. Cl.
  CPC .... *G16C 20/40* (2019.02); *G05B 2219/25061* (2013.01); *G05B 2219/25083* (2013.01); *Y02P 90/02* (2015.11)

(58) Field of Classification Search
  CPC .......... G05B 2219/25061; Y02P 90/02; Y02P 90/16; Y02P 90/18
  See application file for complete search history.

(56) References Cited

U.S. PATENT DOCUMENTS

| | | | | |
|---|---|---|---|---|
| 8,195,401 | B2 * | 6/2012 | Ella | G06Q 50/06 702/13 |
| 8,634,949 | B2 * | 1/2014 | Barker | G06Q 50/04 700/99 |
| 9,256,219 | B2 * | 2/2016 | Blevins | G05B 19/0426 |
| 10,013,149 | B2 * | 7/2018 | Nixon | G05B 23/0216 |
| 10,139,812 | B2 * | 11/2018 | Jones | G05B 19/0426 |
| 10,261,479 | B2 * | 4/2019 | Krasberg | G05B 13/024 |
| 2007/0078540 | A1 * | 4/2007 | Bump | G05B 19/41845 700/90 |
| 2007/0271039 | A1 | 11/2007 | Ella et al. | |
| 2011/0288668 | A1 | 11/2011 | Barker et al. | |
| 2016/0299477 | A1 * | 10/2016 | Krasberg | G05B 13/024 |
| 2019/0121920 | A1 * | 4/2019 | Park | G06F 30/00 |
| 2019/0196418 | A1 * | 6/2019 | Krasberg | G05B 13/024 |

OTHER PUBLICATIONS

International Search Report of PCT/EP2015/077243 dated Jan. 26, 2016.

* cited by examiner

METHOD FOR CONFIGURING A PRODUCTION PLANT DESIGNED FOR PERFORMING AT LEAST ONE CHEMICAL REACTION

CROSS REFERENCE TO RELATED APPLICATIONS

This application is a § 371 National State Application of PCT/EP2015/077243, filed Nov. 20, 2015, which claims priority to German Application No. 10 2014 117 122.5 filed Nov. 24, 2014.

The work which led to this invention was sponsored by grant agreement no. 228867 as part of the European Union's F3 Factory (Flexible, Fast and Future Production Processes) seventh framework program (FP7/2007-2013).

BACKGROUND OF THE INVENTION

Field of the Invention

The present invention relates to a method for configuring a production plant designed for performing at least one chemical reaction.

The invention also relates to a computer program having program code means stored on a computer-readable data storage medium, to a data storage medium and to a computer system.

Description of Related Art

In order to perform a chemical reaction for the purpose of producing a particular chemical product, it is necessary to provide a production plant having an individual plant structure. In order to be able to perform the process steps respectively required in terms of process engineering in individual plant modules, plant modules which are technically suitable for this purpose and have a plurality of part components should be combined with one another to form a production plant.

A multiplicity of plant modules are usually available in a laboratory store, in which case it can generally be assumed that none of these plant modules from the stock directly complies with the process-specific and partly very complex technical requirements for producing a particular chemical product. It is therefore very difficult to use a plant module which is in stock again, with the result that a new plant module which complies with the particular complex technical requirements generally has to be compiled from a multiplicity of part components. Since each new development of plant modules is associated with extra outlay in comparison with the 1:1 reuse of plant modules and the time-reducing effect when planning modular production plants is absent as a result, the selection and configuration of new plant modules should be accelerated with regard to the process to be implemented.

SUMMARY

Therefore, the object of the invention is to provide rapid and inexpensive configuration of a production plant designed for performing at least one chemical reaction.

This object is achieved by means of a method having the features according to patent claim 1, a computer program having the features according to patent claim 8, a data storage medium having the features according to patent claim 9 and a computer system having the features according to patent claim 10. Preferred configurations are stated in the subclaims and may each represent an aspect of the invention per se or in any desired combination with one another.

Claim 1 provides a method for configuring a production plant designed for performing at least one chemical reaction, the production plant having at least one plant module, and a plant module being selected from a module database running on a first server system and/or being compiled from a component database running on a second server system in order to configure the production plant, and the selection and/or compiling of a plant module comprising the following steps:

manual first input of process-specific technical requirements imposed on a plant module to a query mask of the module database and confirmation of the input;

comparison of the first input with at least one technical parameter of the multiplicity of plant modules, which is stored in the module database and defines a process-specific property of a respective plant module, on the first server system and, in the event of a negative result:

identification of at least one plant module, the process-specific property of which does not comply with the process-specific technical requirements, in an output mask of the module database;

identification of at least one part component of the identified plant module which does not comply with the requirements imposed on the plant module, and/or identification of a technical parameter of a series component of the part component of the identified plant module which does not comply with the requirements imposed on the plant module;

manual and/or automatic second input of process-specific technical requirements for the identified part component and/or of the technical parameter of the series component to a query mask of the component database;

comparison of the second input with the technical parameters of the multiplicity of series components, which are stored in the component database and define the process-specific property of a respective series component, and, in the event of a positive result:

identification of at least one series component of a part component, which complies with the process-specific technical requirements, in an output mask of the component database and compiling of the output plant module with the output series component.

DETAILED DESCRIPTION OF A PREFERRED EMBODIMENT

Figure 1:
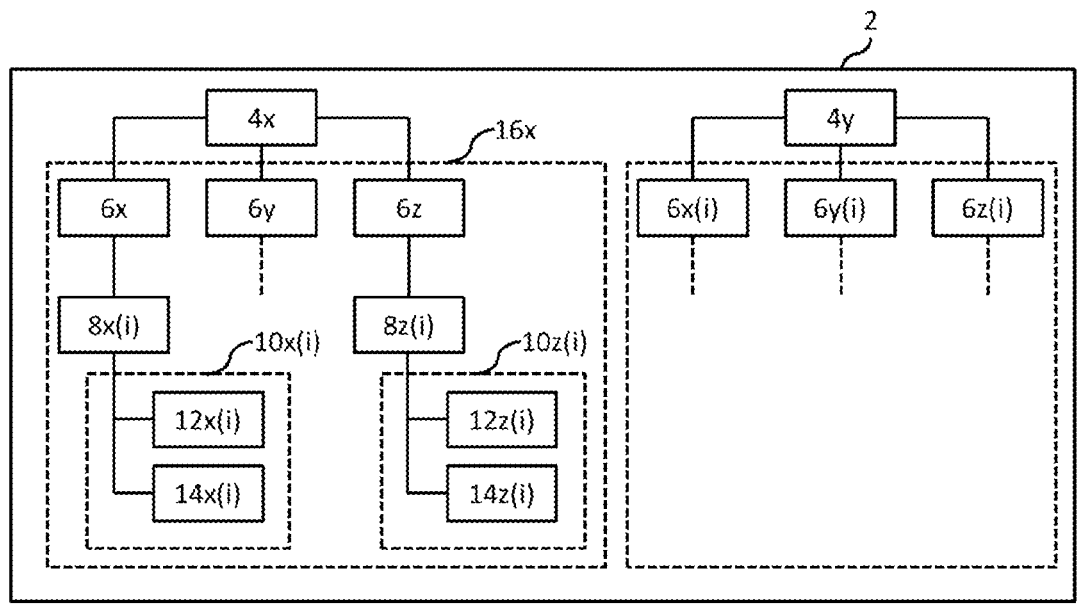
FIGS. 1-3 depict embodiments as described herein.

The module database has a multiplicity of plant modules and each plant module comprises a multiplicity of part components, each part component having a series component with at least one technical parameter, preferably a plurality of technical parameters, defining the process-specific property of the series component. The process-specific property of a plant module comprises at least one technical parameter, preferably a plurality of technical parameters, defining the process-specific property of a series component. In this manner, the process-specific property of a plant module stored in the module database can be clearly defined.

The component database has a multiplicity of part components each with at least one series component, each series component being assigned at least one technical parameter, preferably a plurality of technical parameters, defining a process-specific property of a respective series component.

Process-specific technical requirements imposed on a plant module are understood as meaning a technical parameter which should or must be complied with by the plant module and/or by a part component of the plant module in order to be able to safely perform preferably one chemical reaction in the plant module. However, these technical requirements are particularly preferably a plurality of technical parameters, a first technical parameter preferably being a part-component-specific variable of a part component, and/or a second technical parameter being a series-specific variable of a series component. The first technical parameter and/or the second technical parameter is/are preferably information or values relating to the flow rate and/or the operating pressure and/or the operating temperature and/or the dwell time of a substance in a part component or in the plurality of part components of a plant module. The unit in which the technical parameters are input to the query mask of the module database and/or the query mask of the component database is predefined by the query mask of the module database or the query mask of the component database.

The first input and/or the second input is/are preferably effected via an input module, the input module being connected to the first server system and/or to the second server system using communication technology. The input module is preferably a computer and/or a laptop and/or a tablet.

The query mask of the module database and/or the output mask of the module database and/or the query mask of the component database and/or the output mask of the component database can be displayed on the input module. The display is preferably effected in the form of a table on a screen and/or a monitor of the input module.

One aspect of the invention is therefore that, in a first step, a plant module which complies with the process-specific technical requirements is searched for in the module database. If a plant module which complies with the process-specific technical requirements is not available, at least one plant module which does not comply with the process-specific technical requirements is identified, the part component which does not comply with the requirements and/or the technical parameter of a series component of the part component of the identified plant module which does not comply with the requirements being identified and shown. In this manner, a series component of the part component which complies with the requirements can be searched for in the component database for the identified part component which does not comply with the requirements. If a series component which complies with the requirements is available in the component database, the identified plant module can be adapted by replacing the part component which does not comply with the requirements with the series component of the part component which is identified in the component database and complies with the requirements. This provides a method which enables rapid and inexpensive configuration of the production plant designed for performing at least one chemical reaction.

One preferred further development of the invention provides for the following step to be carried out after a positive comparison of the process-specific technical requirements imposed on a plant module with the technical parameters of the multiplicity of plant modules stored in the module database:

identification of at least one plant module, the process-specific property of which complies with the process-specific technical requirements.

This makes it possible to identify a plant module which complies with the process-specific technical requirements as early as after the first test step, as a result of which the configuration of the production plant designed for performing at least one chemical reaction can be accelerated. If a plant module which complies with the process-specific technical requirements is identified as early as after the first test step, the following test steps are optional. A plant module which does not comply with the process-specific requirements can therefore be additionally identified.

Another preferred further development of the invention provides for the following step to be carried out after a negative comparison of the manual and/or automatic second input of the process-specific technical requirements for the identified part component and/or of the technical parameter of the series component with the technical parameters of the multiplicity of series components stored in the component database:

manual and/or automatic third input of process-specific technical requirements imposed on a plant module to the query mask of the component database;

comparison of process-specific technical requirements imposed on the plant module with the technical parameters of the multiplicity of series components of the part components which are stored in the component database and define the process-specific property of a respective series component;

output of a multiplicity of part components, the process-specific properties of the series components of which comply with the process-specific technical requirements imposed on the plant module; and provision of a plant module which complies with the process-specific technical requirements from the multiplicity of output part components and/or series components.

In this manner, a plant module which complies with the process-specific technical requirements is newly configured from a multiplicity of series components of different part components. A new plant module comprising individual part components is preferably configured only after it has been checked whether a plant module which does not comply with the process-specific technical requirements can be compiled with at least one part component identified from the component database in such a manner that it complies with the process-specific technical requirements imposed on the plant module. This makes it possible to ensure that those plant modules which could be converted with little effort are first of all identified, as a result of which a plant module which complies with the process-specific technical requirements can be provided rapidly and with low costs.

Before a new plant module comprising individual part components is configured, a check is particularly preferably carried out in order to determine whether a plant module which complies with the process-specific requirements is available in the module database. This provides a particularly economical method for selecting a plant module which complies with the process-specific technical requirements.

In principle, the first server system may be a server system which differs from the second server system, the first server system being connected to the second server system using communication technology. However, one preferred further development of the invention provides for the second server system to be an integral part of the first server system. The module database and the component database are therefore arranged on one server system, preferably on the first server.

In principle, the module database may be separate from the component database. This means that there is no connection between the module database and the component database. In this manner, the first input of the process-specific technical requirements imposed on the plant module to the query mask of the module database and the second input of the process-specific technical requirements for the identified part component and/or of the technical parameter of the series component to the query mask of the component database must be input manually. However, provision is particularly preferably made for the component database to be linked to the module database. If the component database is linked to the module database, at least one part of the manual input to the query mask of the module database can be automatically transmitted to the query mask of the component database. A very particularly preferred further development of the invention provides for the component database to be an integral part of the module database. In this manner, as a result of the process-specific technical requirements imposed on the plant module being manually input to the query mask of the module database, an automatic, second input of the process-specific technical requirements for the identified part component to the query mask of the component database can be effected if a plant module which does not comply with the process-specific technical requirements is output and if the part component which does not comply with the requirements imposed on the plant module is identified. Therefore, the operation for configuring a production plant designed for performing at least one chemical reaction can be accelerated. In addition, input errors and/or transmission errors can be reduced as a result of the automatic transmission or input to the query mask of the component database.

Another advantageous further development of the invention provides for a plurality of technical parameters defining the process-specific property of the respective plant module to be assigned to the multiplicity of plant modules stored in the module database, and/or for a plurality of technical parameters defining the process-specific property of the series components to be assigned to the multiplicity of part components which are stored in the component database and have a plurality of series components, and for the plurality of different technical parameters to be checked in successive test steps with the process-specific requirements during comparison of the process-specific requirements imposed on a plant module.

Another preferred further development of the invention provides for at least one technical parameter which defines the process-specific property of the respective plant module and/or at least one technical parameter which defines the process-specific property of the series components to be a hard test criterion or a soft test criterion, those technical parameters which are a hard test criterion being given preference over those technical parameters which are a soft test criterion when comparing the process-specific requirements imposed on the plant module. A hard test criterion preferably relates to those technical parameters of a part component or of a series component of a part component which imperatively have to be complied with in order to comply with the process-specific requirements and/or relates to a part component which can be replaced only with a very large amount of effort. As a result of the preferred testing of the hard test criteria, plant modules in which a part component can be replaced with little effort in order to provide a plant module which complies with the process-specific requirements can be identified in a particularly effective manner.

Another advantageous further development of the invention provides for the process-specific technical requirements to be defined by a process-specific parameter limit value, the exceeding or undershooting of which results in the process-technical requirement being complied with, or by a process-specific parameter range, the compliance with which results in the process-technical requirement being complied with.

Another advantageous further development of the invention is that the process-specific technical requirements take into account whether
- a mass throughput needed to perform a particular chemical reaction is possible in a plant module and/or in a part component of a plant module, and/or
- a dwell time in a plant module and/or in a part component of a plant module is permissible for performing a particular chemical reaction, and/or
- an operating pressure and/or a pressure loss of a plant module and/or of a part component of a plant module is/are permissible for performing a particular chemical reaction, and/or
- a heat transfer capacity of a plant module and/or of a part component of a plant module is permissible for performing a particular chemical reaction, and/or
- suitable kinetics of the reaction and mixing are present in a plant module and/or in a part component of a plant module while a particular chemical reaction is being performed, and/or
- thermally safe operation of a plant module and/or of a part component of a plant module is ensured while a particular chemical reaction is being performed, and/or
- a temperature at a hotspot of a plant module and/or of a part component of a plant module is permissible for performing a particular chemical reaction, and/or
- sufficiently intensive initial mixing of educts by means of a plant module and/or a part component of a plant module can be achieved while a particular chemical reaction is being performed, and/or
- a risk, such as preferably thermal decomposition and/or oxidative spontaneous ignition and/or a fire and/or the formation of an explosive atmosphere and/or a health risk, is present for using a substance for performing at least one chemical reaction in a plant module and/or in a part component.

Which of these process-specific technical requirements are taken into account depends on the respective conditions, requirements and technical configurations of the plant modules.

The invention also relates to a computer program having program code means which are stored on a computer-readable data storage medium and cause a computer and/or a server and/or a corresponding computing unit to carry out a method according to one of the above-mentioned configurations or any desired combination thereof when they are executed on the computer or the corresponding computing unit. The advantages mentioned above with reference to the method are accordingly associated with this computer program.

The invention also relates to a data storage medium having an above-mentioned computer program. The advantages mentioned above with reference to the method and the computer program are accordingly associated with this data storage medium.

The invention also relates to a computer system on which an above-mentioned computer program is loaded. The advantages mentioned above with respect to the method and the computer program are accordingly associated with this computer system.

Figure 2:
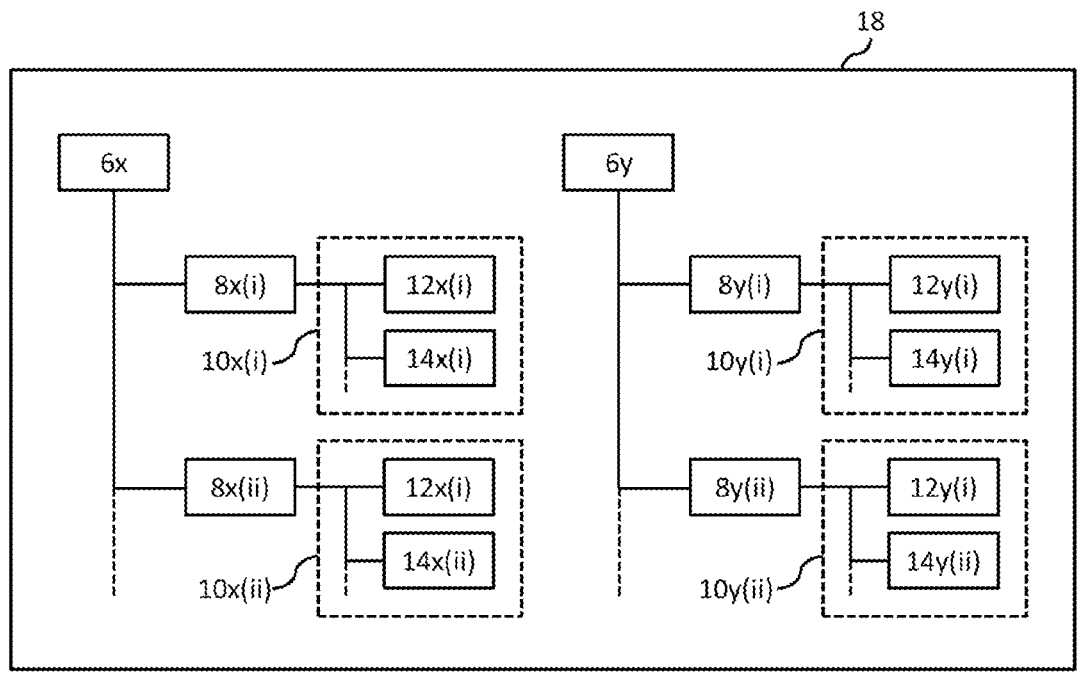
Figure 3:
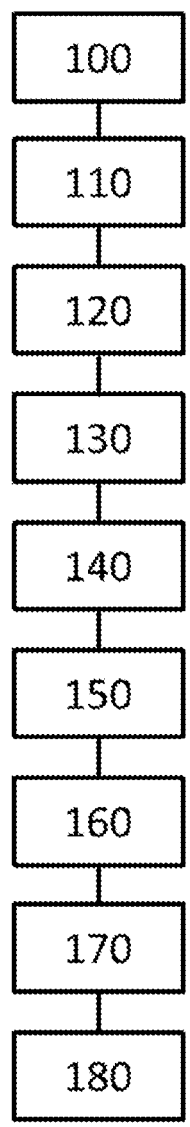

The invention is explained by way of example below with reference to the attached figures using preferred exemplary embodiments, the features described below being able to represent an aspect of the invention both each per se and in combination with one another. In the figures:

FIG. 1: shows a module database according to one preferred exemplary embodiment of the invention, FIG. 2: shows a component database according to the preferred exemplary embodiment of the invention, and FIG. 3 shows a method for configuring a production plant designed for performing at least one chemical reaction according to the preferred exemplary embodiment of the invention.

FIG. 1 shows a module database 2 which is installed on a first server system. The module database 2 comprises a multiplicity of plant modules $4x$, $4y$, each plant module $4x$, $4y$ having a plurality of part components $6x$, $6y$, $6z$, $6x(i)$, $6x(i)$, $6z(i)$. Each part component $6x$, $6y$, $6z$ corresponds to a series component $8x(i)$, each series component $8x(i)$ having a plurality of technical parameters $12x(i)$, $14x(i)$ defining a process-specific property of the series component $10x(i)$. In the present case, a first technical parameter $12x(i)$ is a part-component-specific variable of the part component $6x$ and the second technical parameter $14x(i)$ is a series-specific variable of the series component $8x(i)$. A process-specific property of a plant module $16x$ therefore comprises a plurality of technical parameters defining the process-specific property of a respective series component $10x(i)$ to $10z(i)$.

Using a specific example, this means that the part component $6x$ of the plant module $4x$ is a pump. The series component $8x(i)$ of the pump is then preferably a diaphragm pump having a conveying capacity A. The process-specific property of the diaphragm pump $10x(i)$ is defined by the technical parameters allocated to the diaphragm pump, the first technical parameter $12x(i)$ being a part-component-specific variable of the pump and the second technical parameter $14x(i)$ being a series-specific variable of the diaphragm pump.

FIG. 2 shows a component database 18 which is installed on a second server system. The component database 18 has a multiplicity of part components $6x$, $6y$, each part component $6x$, $6y$ comprising a plurality of series components $8x(i)$, $8x(ii)$, $8y(i)$, $8y(ii)$. Each series component $8x(i)$, $8x(ii)$ is assigned a plurality of technical parameters defining the process-specific property of a respective series component $10x(i)$, $10x(ii)$. The component database 18 therefore comprises different part components $6x$, $6y$ with different series components $8x(i)$, $8x(ii)$, $8y(i)$, $8y(ii)$ in each case.

FIG. 3 shows a method for configuring a production plant designed for performing at least one chemical reaction. The production plant is composed of a plurality of plant modules, preferably reaction modules and/or storage modules, a reaction module being selected from the module database running on the first server system or being compiled from the component database running on the second server system in the present case in order to configure the production plant.

In the present case, the second server system is an integral part of the first server system, with the result that the module database and the component database run on one server system. In addition, the component database and the module database are linked to one another.

In a first method step 100, a manual first input of process-specific technical requirements imposed on the reaction module to a query mask of the module database is first of all effected on an input module connected to the server system using communication technology, the input module being a computer, and the input is confirmed. The process-specific technical requirements imposed on the reaction module are technical parameters such as preferably information on the throughput, the maximum and/or minimum permitted operating pressure, the maximum and/or minimum permitted operating temperature and the minimum required and/or maximum permitted dwell time. This makes it possible to state parameter limit values and parameter ranges in order to define the process-specific technical requirements imposed on the reaction module.

In a second method step 110, the first input is compared with the technical parameters which are stored in the module database and define the process-specific property of a respective reaction module. In this case, a check is carried out in order to determine whether a reaction module which complies with the process-specific technical requirements imposed on the reaction module for configuring the production plant is available in the module database. The process-specific properties of a respective reaction module are defined by the respective process-specific property of the series component of the different part components of a reaction module.

The different part components of a reaction module stored in the module database also have different priorities. Part components which have a great influence on an energy balance and/or mass balance of the reaction module have a higher priority than components with low influences. Part components with a high prioritization are preferably a main apparatus and/or a conveying device. Part components with a low prioritization are preferably components of the sensor system and/or actuator system and/or the local pipework.

In a third method step 120, in the event of a positive comparison, at least one reaction module, the process-specific property of which complies with the process-specific technical requirements, is identified. In the event of a negative comparison in which a reaction module which complies with the process-specific technical requirements cannot be determined in the module database, a reaction module which does not comply with the process-specific technical requirements is identified in an output mask of the module database. In this case, the reaction module is selected on the basis of the prioritization of the part components, with the result that a reaction module, the part components of which with a high prioritization comply with the process-specific technical requirements of the reaction model and at least one part component with a low priority does not comply with the process-specific technical requirements of the reaction model, is identified.

That part component of the identified reaction module which does not comply with the requirements imposed on the reaction module is identified and a technical parameter of the series component of the part component of the identified reaction module which does not comply with the requirements imposed on the reaction module is identified in the output mask of the module database.

In a fourth method step 130, a manual second input of process-specific technical requirements for the identified part component to a query mask of the component database is effected on the computer and the input is confirmed.

In a fifth method step 140, the second input is compared with the technical parameters of the multiplicity of series components which are stored in the component database and define the process-specific property of a respective series component.

In a sixth method step 150, in the event of a positive comparison, at least one series component of a part component which complies with the process-specific technical requirements is identified. In this manner, the reaction module which does not comply with the process-specific requirements can be configured with the identified series component in order to provide a reaction module which complies with the process-specific requirements.

In the event of a negative comparison, a manual third input of the process-specific technical requirements imposed on the reaction module to the query mask of the component database is effected on the computer in a seventh method step 160.

In an eighth method step 170, the process-specific technical requirements imposed on the reaction module are compared with the technical parameters of the multiplicity of series components of the different part components which are stored in the component database and define the process-specific property of a respective series component.

In a ninth method step 180, a multiplicity of part components, the process-specific properties of the series components of which comply with the process-specific technical requirements imposed on the reaction module, are output on the output mask of the component database. In addition, a reaction module which complies with the process-specific technical requirements is provided from the multiplicity of output part components and/or series components.

This provides a method in which a check is first of all carried out in order to determine whether a reaction module from the stock meets the technical requirements of a reaction module for configuring a new production plant. If this is not the case, a check is carried out in order to determine whether an already existing reaction module could be converted with a small amount of effort, preferably by replacing a part component, in order to provide in this manner a reaction module which complies with the process-specific technical requirements. If this is also not possible, a new reaction module having part components from the component database is provided.

This provides a method which enables rapid and inexpensive configuration of a production plant designed for performing at least one chemical reaction.

REFERENCE SYMBOLS (EXCEPT FOR REFERENCE SYMBOLS FROM NUMBER 100 ON WHICH REPRESENT METHOD STEPS)

2 Module database
4 Plant module
6 Part component
8 Series component
10 Process-specific property of the series component
12 First technical parameter
14 Second technical parameter
16 Process-specific property of the plant module
18 Component database

The invention claimed is:

1. A method for configuring a production plant designed for performing at least one chemical reaction, the production plant having at least one plant module, comprising:

a) selecting the at least one plant module from a module database running on a first server system, wherein a) comprises:

a.1) manually inputting a first set of process-specific technical requirements imposed on the plant module to a query mask of the module database and confirming the inputting;

a.2) comparing the first set of process-specific technical requirements with at least one technical parameter of a multiplicity of plant modules on the first server system, wherein the at least one technical parameter is stored in the module database and defines a process-specific property of a respective plant module, a.3) in the event of a negative result, wherein a negative result comprises a determination that the process-specific property of the respective plant module does not comply with the first set of process-specific technical requirements:

a.3.i) identifying at least one plant module, the process-specific property of which does not comply with the process-specific technical requirements, in an output mask of the module database; and a.3.ii) identifying at least one part component of the identified plant module from a.3.i) which does not comply with the requirements imposed on the plant module; or identifying the at least one technical parameter of a series component of the part component of the identified plant module from a.3.i) which does not comply with the requirements imposed on the plant module; or identifying both at least one part component of the identified plant module and the at least one technical parameter of the series component of the identified plant module from a.3.i);

or b) compiling the at least one plant module from a component database running on a second server system, wherein b) comprises:

b.1) manually, automatically, or manually and automatically inputting a second set of process-specific technical requirements for a technical parameter of a series component to a query mask of the component database;

b.2) comparing the second set of process-specific technical requirements with at least one technical parameter of a multiplicity of series components, wherein the at least one technical parameter is stored in the component database and defines a process-specific property of a respective series component;

b.3) in the event of a positive result, wherein a positive result comprises a determination that the process-specific property of the identified plant module complies with the second set of process-specific technical requirements:

b.3.i) identifying at least one series component of a part component, which complies with the process-specific technical requirements, in an output mask of the component database and compiling the output plant module with the output series component;

or c) selecting the at least one plant module from the module database running on the first server system and compiling the at least one plant module from the component database running on the second server system, wherein c) comprises:
    c.1) manually inputting a first set of process-specific technical requirements imposed on the plant module to a query mask of the module database and confirming the inputting;
    c.2) comparing the first set of process-specific technical requirements with at least one technical parameter of a multiplicity of plant modules on the first server system, wherein the at least one technical parameter is stored in the module database and defines a process-specific property of a respective plant module,
    c.3) in the event of a negative result, wherein a negative result comprises a determination that the process-specific property of the respective plant module does not comply with the first set of process-specific technical requirements:
        c.3.i) identifying at least one plant module, the process-specific property of which does not comply with the process-specific technical requirements, in an output mask of the module database; and
        c.3.ii) identifying at least one part component of the identified plant module from c.3.i) which does not comply with the requirements imposed on the plant module; or identifying a technical parameter of a series component of the part component of the identified plant module from c.3.i) which does not comply with the requirements imposed on the plant module; or identifying both at least one part component of the identified plant module and the technical parameter of the series component of the identified plant module from c.3.i);
        c.3.iii) manually, automatically, or manually and automatically inputting a second set of process-specific technical requirements for the identified part component from c.3.ii) to a query mask of the component database;
        c.3.iv) comparing the second set of process-specific technical requirements with at least one technical parameter of a multiplicity of series components, wherein the at least one technical parameter is stored in the component database and defines a process-specific property of a respective series component;
        c.3.v) in the event of a positive result after c.3.iv), wherein a positive result comprises a determination that the process-specific property of the identified plant module complies with the second set of process-specific technical requirements, identifying at least one series component of a part component, which complies with the process-specific technical requirements, in an output mask of the component database and compiling the output plant module with the output series component.

2. The method as claimed in claim 1, wherein after a positive comparison in a.2) of process-specific technical requirements imposed on a plant module with the technical parameters of the multiplicity of plant modules stored in the module database, the method further comprises:
    a.2.i) identifying at least one plant module, the process-specific property of which complies with the process-specific technical requirements;
    or wherein after a positive comparison in c.2) of process-specific technical requirements imposed on a plant module with the technical parameters of the multiplicity of plant modules stored in the module database, the method further comprises:
    c.2.i) identifying at least one plant module, the process-specific property of which complies with the process-specific technical requirements.

3. The method as claimed in claim 1, wherein after a negative comparison in b.2) of the second set of process-specific technical requirements for the technical parameter of the series component with technical parameters of the multiplicity of series components stored in the component database, the method further comprises:
    b.2.i) manually, automatically, or manually and automatically inputting a third set of process-specific technical requirements imposed on the plant module to the query mask of the component database;
    b.2.ii) comparing the third set of process-specific technical requirements imposed on the plant module with the technical parameters of a multiplicity of series components of the part components which are stored in the component database and which define the process-specific property of a respective series component;
    b.2.iii) outputting a multiplicity of part components, the process-specific properties of the series components of which comply with the process-specific technical requirements imposed on the plant module; and
    b.2.iv) identifying a plant module which complies with the process-specific technical requirements from the multiplicity of output part components and/or series components;
    or wherein after a negative comparison in c.3.iv) of the second set of process-specific technical requirements for the identified part component from c.3.ii), the method further comprises:
    c.3.vi.1) manually, automatically, or manually and automatically inputting a third set of process-specific technical requirements imposed on the plant module to the query mask of the component database;
    c.3.iv.2) comparing the third set of process-specific technical requirements imposed on the plant module with the technical parameters of the multiplicity of series components of the part components which are stored in the component database and which define the process-specific property of a respective series component;
    c.3.iv.3) outputting a multiplicity of part components, the process-specific properties of the series components of which comply with the process-specific technical requirements imposed on the plant module; and
    c.3.iv.4) identifying a plant module which complies with the process-specific technical requirements from the multiplicity of output part components and/or series components.

4. The method as claimed in claim 1, wherein in a.2), b.2), c.2), or any combination thereof, there is a plurality of technical parameters, and the plurality of technical parameters checked in successive test steps with the process-specific requirements during comparison of the process-specific requirements imposed on a plant module.

5. The method as claimed in claim 1, wherein the process-specific technical requirements are defined either by a process-specific parameter limit value, the exceeding or undershooting of which results in the process-technical requirement being complied with, or by a process-specific parameter range, the compliance with which results in the process-technical requirement being complied with.

6. The method as claimed in claim 1, the process-specific technical requirements taking into account whether a mass throughput needed to perform a particular chemical reaction is possible in a plant module, in a part component of a plant module, or in a plant module and a part component of a plant module a dwell time in a plant module, in a part component of a plant module, or in a plant module and a part component of a plant module is permissible for performing a particular chemical reaction, an operating pressure, a pressure loss of a plant module and/or of a part component of a plant module, or operating pressure and a pressure loss of a plant module and/or of a part component of a plante module is/are permissible for performing a particular chemical reaction, a heat transfer capacity of a plant module, of a part component of a plant module, or of a plant module and of a part component of a plant module is permissible for performing a particular chemical reaction, suitable kinetics of the reaction and mixing are present in a plant module, in a part component of a plant module, or in a plant module and in a part component of a plant module while a particular chemical reaction is being performed, thermally safe operation of a plant module, of a part component of a plant module, or of a plant module and of a part component of a plant module is ensured while a particular chemical reaction is being performed, a temperature at a hotspot of a plant module, of a part component of a plant module, or of a plant module and of a part component of a plant module is permissible for performing a particular chemical reaction, sufficiently intensive initial mixing of educts by a plant module, a part component of a plant module, or a plant module and a part component of a plant module can be achieved while a particular chemical reaction is being performed, a risk, optionally thermal decomposition, oxidative spontaneous ignition, a fire, the formation of an explosive atmosphere, a health risk, or any combination thereof, is present for using a substance for performing at least one chemical reaction in a plant module, in a part component, or in a plant module and in a part component, any combination of the above.

7. A computer program having program code which are stored on a non-transitory computer-readable data storage medium and cause a computer or a corresponding computing unit to carry out a method as claimed in claim 1, when executed on the computer or the corresponding computing unit.

8. A non-transitory data storage medium having a computer program as claimed in claim 7.

9. A computer system on which a computer program as claimed in claim 7 is loaded.

* * * * *